United States Patent [19]

Farina et al.

[11] 4,244,694
[45] Jan. 13, 1981

[54] REACTOR/SEPARATOR DEVICE FOR USE IN AUTOMATED SOLID PHASE IMMUNOASSAY

[75] Inventors: Peter R. Farina, North Salem; Kathy P. Ordonez, Peekskill; Iris J. Siewers, White Plains, all of N.Y.

[73] Assignee: Union Carbide Corporation, New York, N.Y.

[21] Appl. No.: 892,321

[22] Filed: Mar. 31, 1978

[51] Int. Cl.² .................... G01N 33/16; G01N 31/06
[52] U.S. Cl. .................... 23/230 B; 23/230.6; 23/915; 23/920; 210/198.1; 422/72; 424/1; 424/12; 435/7
[58] Field of Search .................... 23/230 B, 230.6, 915, 23/920; 424/1, 12; 422/72

[56] References Cited

U.S. PATENT DOCUMENTS

| | | | |
|---|---|---|---|
| 3,918,909 | 11/1975 | Arlman | 23/230 B X |
| 3,953,172 | 4/1976 | Shapiro | 23/230 R |
| 3,961,894 | 6/1976 | Gordon | 23/230.6 |
| 4,039,652 | 8/1977 | Adams | 424/1 |
| 4,059,685 | 11/1977 | Johnson | 424/1 X |
| 4,128,628 | 12/1978 | Brooker | 424/1 |
| 4,151,254 | 4/1979 | Gimovsky | 422/71 |
| 4,170,454 | 10/1979 | Meriadec | 23/230.6 |

OTHER PUBLICATIONS

G. Ertingshausen et al., Clin. Chem., 21(9), 1305–1313, (1975).

*Primary Examiner*—Sidney Marantz
*Attorney, Agent, or Firm*—William Raymond Moran

[57] ABSTRACT

A reactor/separator device is provided for use in automated solid phase immunoassay. The device is a column, fitted at the bottom portion thereof with a water impermeable disc which can hold immunoabsorbents immobilized antisera, ion exchange resins and the like. When the contents of the column supported by the disc are brought into contact with an aqueous phase containing reagents or reactants by centrifugal force, a chemical reaction is initiated. After reaction, centrifugally applied pressure forces the aqueous phase through the filter disc making it water permeable and separating a desired component for subsequent analysis.

9 Claims, 2 Drawing Figures

REACTOR/SEPARATOR DEVICE FOR USE IN AUTOMATED SOLID PHASE IMMUNOASSAY

This invention relates in general to a reactor/separator device useful in automated solid phase immunoassay. In another aspect, this invention is directed to a process for conducting radioimmunoassays which utilize a column containing a disc which is impermeable to liquids at low pressures, but permeable to liquids at higher pressures in a centrifugal field.

The introduction of radioimmunoassay (RIA) in 1959 by Yalow and Berson (1) as a diagnostic tracer technique to replace the slow bioassay methods then in use has revolutionized many areas of clinical testing and research, owing to its specificity and extreme sensitivity.
(1) Nature, 184, 1648 (1959)

The RIA technique is based on the ability of an antibody and a specific antigen to form a reversible antigen-antibody complex. The assay is performed by adding a fixed quantity of radiolabeled antigen to samples which contain antiserum and known amounts of "standard" antigen. During incubation, radiolabeled antigen and unlabeled antigen compete for a limited number of binding sites on the antibody. After incubation, antibody-bound antigen is separated from the free antigen and the ratio of free to bound can be plotted on a dose-response curve. An unknown serum sample can then be assayed by the same procedure and the concentration of antigen determined by referring to the standard dose-response curve.

Frequently, the classical methods of RIA are cumbersome, time consuming and have error-producing steps because of the requirements of multiple pipettings and test tubes, duplicate assays, prolonged incubation times and difficult, inefficient separation procedures.

Prior to the present invention there were several devices known in the prior art for performing saturation analysis. For example, U.S. Pat. No. 3,918,909 which issued Nov. 11, 1975, describes a device comprised of a tubular member, open at both ends and containing at the upper end a reaction compartment. A hydrophobic filter is located at the base of the reaction compartment and above a separation chamber located below. In performing the analysis, the reactants are mixed and incubated in the upper chamber, then transferred to the lower chamber through the filter by shaking or applying a pressure differential between the upper and lower chambers. In the lower chamber, the separation agent separates a radioactive substance bound to a competitive binder from its unbound form. In contrast to the present invention, the device is not directly applicable to automated solid phase immunoassay nor does it employ centrifugal force. Moreover, the reaction and separation are conducted in separate chambers.

U.S. Pat. Nos. 3,961,894 which issued Apr. 22, 1974, and 4,039,652 which issued Aug. 2, 1977, both describe a method for determining substances in fluid samples utilizing a device comprising a column containing an insoluble porous matrix with immobilized binding partners to the substance being analyzed.

The device is a cylindrical body having a fixed geometry and terminating at one end in a tapered tip. In the lower portion of the column is a porous polyethylene disc which supports the matrix. In U.S. Pat. No. 4,039,652 it is stated that the flow characteristics of the solid phase preferentially be such that it exhibits a sponge-like fluid retention property under the influence of gravity. Fluid retained in the matrix may then be displaced by adding additional fluid to the device. Thus, once a fluid phase is added to the solid phase and retained thereby, the phases are effectively in a state of incubation until another fluid, such as a buffer, is added to displace the retained fluid. While these devices provide a means for conducting incubation and separation in one chamber, they do not employ a water impermeable disc nor centrifugal components.

Accordingly, one or more of the following objects will be achieved by the practice of this invention. It is an object of this invention to provide a reactor/separator device which is useful in immunoassay systems. Another object of this invention is to provide a device which is utilized in an analytical system wherein centrifugal force is employed for mixing, transferring and separation of reactants. A further object is to provide a reactor/separator device which is fitted at its bottom with a water impermeable disc. A still further object of the invention is to provide a device for use in automated solid-phase radioimmunoassay wherein the reaction and separation are conducted in the same chamber. Another object is to provide a device wherein the water-impermeable retaining disc is rendered permeable by increasing the centrifugal force. A further object is to provide reactor/separator devices which can be transported and stored safely until ready for use. A still further object of this invention is to provide a process for conducting immunoassay employing the separator/reactor devices. These and other objects will readily become apparent to those skilled in the art in the light of the teachings herein set forth.

The objects of the invention and the preferred embodiments thereof will best be understood by reference to the accompanying drawings wherein.

Figure 1:
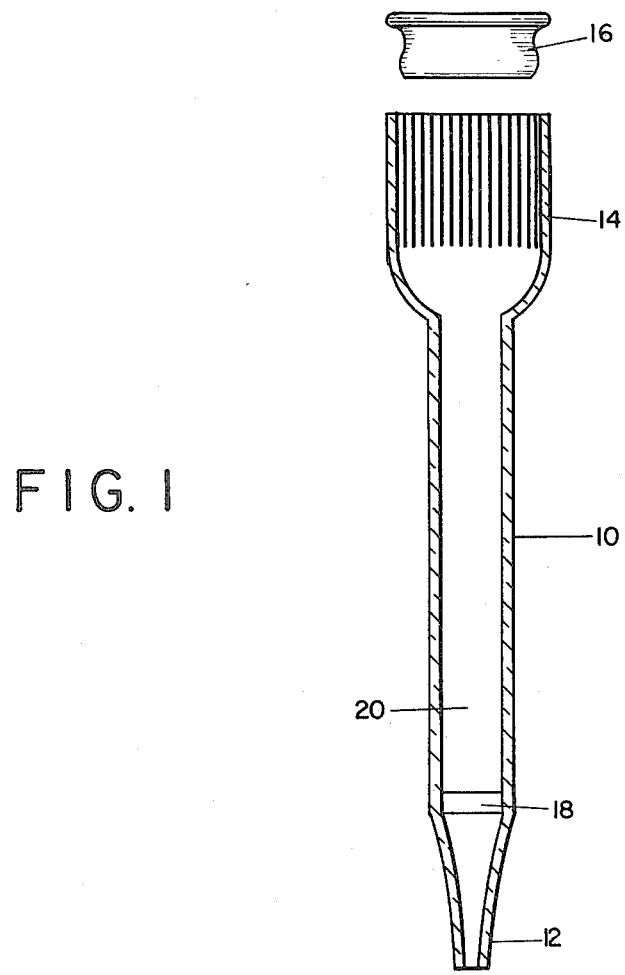
FIG. 1 is a cross-sectional view of the reactor/separator device of this invention.

With further reference to the drawings, FIG. 1 depicts in cross-sectional view a reactor/separator device of this invention. The column 10 can be comprised of most any inert material such as glass, plastic and the like. A preferred material is polystyrene which is transparent light and not easily broken. Column 10 is approximately 4 inches long and has an outer barrel diameter of about 0.4 inches. It can contain approximately 2.5 milliliters of liquid. The tip 12 has an internal diameter of about 0.04 inches and the top reservoir 14 has an outer diameter of about 0.8 inches. Stopper 16 seals the top of the column. Retaining disc 18 is a filter which is impermeable to liquids at atmospheric and low centrifugal forces but is permeable to liquids at high centrifugal forces. Reaction chamber 20 contains the immobilized reagent and incubate.

Figure 2:
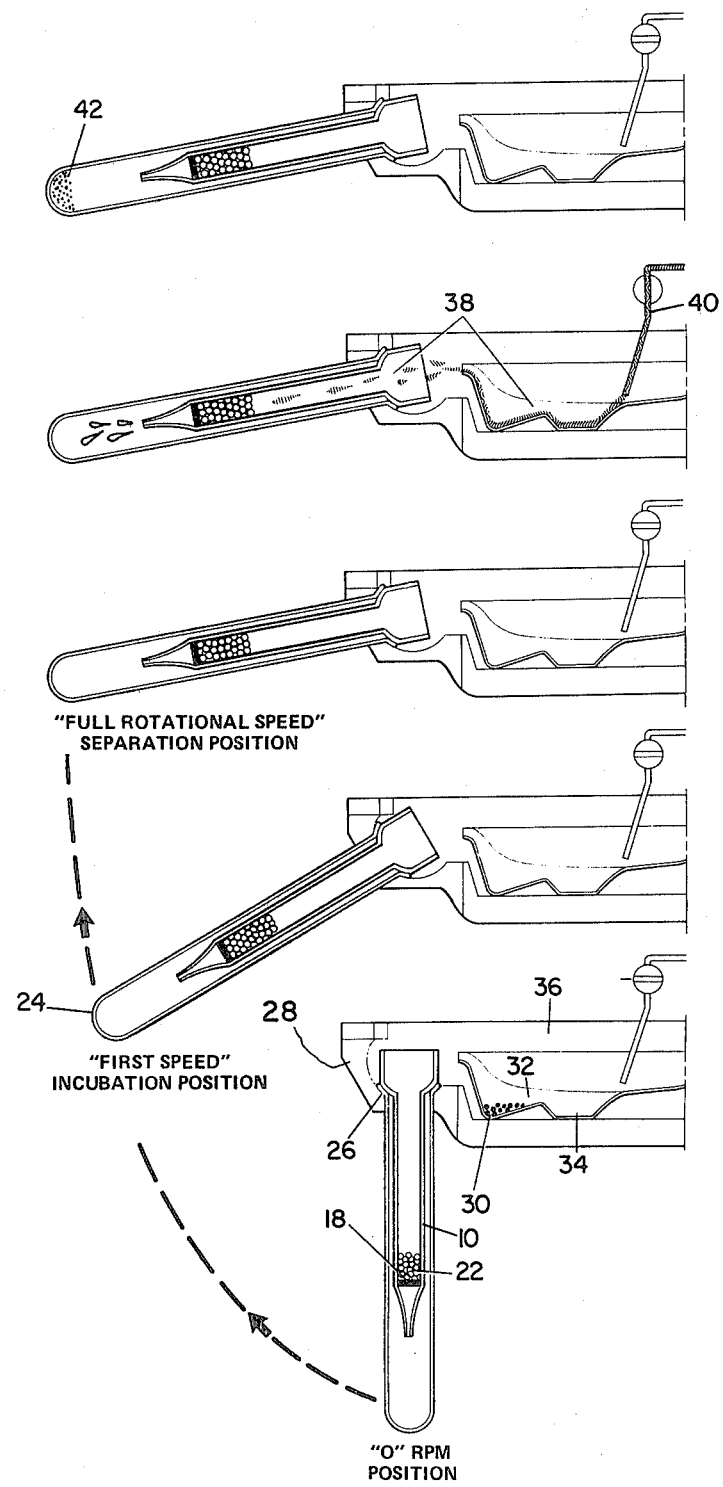
FIG. 2 is a cross-sectional view depicting from bottom to top the sequential reaction, incubation and separation functions of one reactor/separator device contained on a commercially available instrument for assaying liquid materials.

FIG. 2 is a cross-section view of one of the reactor/separator columns 10 fitted with a water impermeable filter disc 18 and charged with a quantity of immobilized antiserum in a dry matrix 22. The columns containing the reactant are positioned in test tubes 24 which in turn are suspended by their rims in ball seats 26 in a plastic ring 28. Serum samples and other reagents 30 are placed in the cavities 32 and 34 of a transfer disc 36 which in turn is placed on a turntable of the Centria[2]

System and automatically keyed so that each cavity is aligned with the opening of the corresponding reactor/separator column. A motor is activated such that a given acceleration the centrifugal force developed transfer simultaneously all the samples and reagents to the reactor/separator column containing the immobilized reactant 22. In the case where the immobilized reactant is entrapped in a dehydrated matrix such as polyacrylamide, a rapid rehydration occurs simultaneously with reaction. After a suitable incubation time has elapsed, the motor is accelerated to a higher velocity followed by the application of a suitable eluent 38 which exerts sufficient hydrostatic pressure to convert the water impermeable filter to one which is freely permeable. This is accomplished by dispensing a stream of suitable liquid e.g., buffer solution, from a reservoir via an eluant pump not shown through a conduit 40 and dispenser into the cavities 32 and 34 of the rapidly turning transfer disc. The pump provides a fixed flow rate of eluant for a fixed period of time and the total eluant quantity is automatically divided by the partitions in the disc which guide the flow into the reactor/separator column. All components 42 which are water soluble and not bound to the immobilized reactant pass freely through the filter and are collected in the test tubes. In this instance where a reagent employed is radioactive, each tube can be removed from the supporting ring and the radioactivity of the contents measured. Assays using the instant invention in conjunction with the Centria System have been conducted in 7 minutes. This permits the user to do kinetic solid phase assays (non-equilibrium conditions)-a process which would be extremely difficult by other conventional methods.

[2]Trademark for an immunoassay apparatus marketed by Union Carbide Corporation.

In its broad aspect, the invention is directed to a reactor/separator device and a process for its use in rapid automated solid phase immunoassay. The device is comprised of, in combination:
(a) a column which is open at both ends,
(b) a retaining and filtering means disposed in the column and which is impermeable to aqueous solutions at approximately atmospheric pressure, but permeable to aqueous solutions when subjected to a centrifugal force, and
(c) a reaction and separation chamber disposed above the retaining and filtering means and contained therein a matrix for the immobilization of at least one antigen-antibody system.

The device of this invention when used in conjunction with analytical instruments which utilize centrifugal force, permits the extension of the capabilities of the apparatus to automated solid phase immunoassay, affinity chromatography and various applications based on contacting or reacting two or more substances followed by a separation.

Multistation analytical devices which utilize a centrifugal field have recently become available for the rapid microanalysis of a wide variety of liquids, such as body fluids, e.g., blood serum, food products and the like. For example, one such instrument which has been developed to automate radioimmunoassay is marketed by Union Carbide Corporation under the trademark "Centria". The Centria System offers several interesting features for performing solution phase immunoassays. The system consists of: (a) an automated pipettor which dispenses samples and reagents, (b) the key module, an incubator/separator in which centrifugal force is used to initiate and terminate multiple radioassay incubations and separations simultaneously, and (c) a gammacounter/computer which counts three tubes simultaneously and converts counts into concentration units. Further description and use of the Centria System is disclosed in U.S. Pat. No. 3,953,172 which issued Apr. 27, 1976, to S. I. Shapiro and G. Ertingshausen and is assigned to the same assignee as this invention. As indicated in this patent, the system utilizes adsorption columns to separate the components to be analyzed.

As previously indicated, the reactor/separator device of this invention is a column fitted with a water impermeable retaining and filtering means which can hold reagents such as immobilized antisera, enzymes, immunosorbents, ion exchangers and the like. The contents of the column can be brought into contact by centrifugal force, or manual addition, with an aqueous phase containing reagents or reactants. After a suitable incubation period, centrifugal force is applied to the column which forces the aqueous phase through the filtering means making it water permeable. This transformation results in the separation of water insoluble phase from a soluble phase, either of which can be subsequently collected and analyzed.

In practice, the retaining and filtering means is in the form of a disc which can be prepared from a variety of porous sheetings. Such materials can be polyethylene, polypropylene, teflon, or the like. In addition, inorganic materials such as glass and ceramic can be used equally well in the instant invention. In the illustrative examples, polyethylene sheeting of approximately one-sixteenth inch in thickness and having a porosity of $25 \pm 3$ microns was employed. Porosities of from about 25 to about 150 and preferably from 25 to 40 microns can be used. Discs of 0.310–0.316 outside diameter were cut from the sheeting and fitted with a seating tool into the lowest section of the column barrel.

The columns themselves can be comprised of most any material such as glass, plastic and the like. A preferred material is polystyrene which is transparent, light, durable and can be effectively used if desired to immobilize antisera, enzymes and affinity ligands by physical adsorption or covalent methodologies. A column designed for use with the Centria System is approximately 4 inches in length and has an outer barrel diameter of about 0.4 inches. It can contain approximately 2.5 milliliters of liquid. The tip has an external diameter of about 0.04 inches and the top reservoir has an outer diameter of 0.8 inches. Other columns can be readily prepared of a size smaller or larger than the one described above.

As previously indicated, the retaining and filtering means is impermeable to aqueous solutions at atmospheric pressure. It is also impermeable to solutions at low pressures of a centrifugal field. Thus, it is possible to mix and transfer samples and reagents to a column by centrifugal force without any passage of liquid through the filter disc. Only upon increasing the centrifugal force will the disc become permeable.

For instance, it has been found that when the reactor/separator devices are used with a transfer disc of the Centria System having a radius of 13 centimeters, that the filter disc is impermeable to liquids at speeds of 100 rpm or below, but becomes permeable with addition of eluants at sustained speeds of 200 rpm and above. The centrifugal force applied to cause the disc to become permeable will, of course, be a function of the speed of the instrument and the distance of the device from the center of rotation.

A unique feature of the reactor/separator of this invention is that is can be employed in several useful modes. For example, the device can be used as a reaction chamber where one or more of the reactants such as antibodies, enzymes, proteins, affinity ligands, ion exchangers, or cells are fixed to the wall of the column. It can also be used as a reaction chamber containing one or more reactants immobilized in or on a matrix or support such as polyacrylamide, Sepharose, agarose, other natural materials, synthetic polymers, or inorganic materials such as glass and ceramics. The matrix, for example, can be in the form of a dehydrated gel, a rigid matrix, beads or powders. Additionally, it can be used as a chamber for reactions involving microorganisms, viruses, red blood components, tissues and the like. Also the device is useful as a reaction chamber where the admixing of two or more solutions result in an insoluble phase one of which must be subsequently filtered.

The devices of this invention can be well utilized for solid phase immunoassays of both short and long duration. However, they are most advantageous for reaction times of very short duration i.e., less than 5 minutes and in particular, where two phases must be separated rapidly. It is at these short reaction times that manual methods are not sufficiently rapid to process multiple samples. And in particular kinetic assays wherein two phases must be separated rapidly.

The novel reactor/separator device can be effectively used to carry out an enzymatic pretreatment step to free bound analyte from serum proteins and simultaneously conduct an immunoassay. Such a process can be accomplished in the following manner: for example, the reactor/separator is charged with a portion of a dehydrated polyacrylamide entrapped antiserum having pores sufficiently small when hydrated to exclude medium and low molecular weight enzymes or proteins. Admixed with the immobilized antiserum is a sufficient quantity of a proteolytic enzyme which can denature or hydrolyze a serum protein which binds the analyte of interest. Serum samples and radiolabels are centrifugally transferred into the reactor/separator. Upon hydration of the gel and solubilization of the enzyme two processes commence: the release of protein bound analyte, and its diffusion and binding to the antiserum in the gel matrix. After a predetermined period of time the elution of enzyme, unbound analyte and radiolabel is accomplished. Alternatively, if the proteolytic enzyme is most stable in aqueous solution then the pretreatment step can be accomplished successfully by placing the enzyme and serum samples in the inner and outer wells of the transfer disc. When the motor is accelerated the reagents are simultaneously mixed and transferred to the reactor/separator column where incubation takes place.

The reactor/separator devices prepared in accordance with the teachings of this invention have been found to be idealy suited for use with the Centria System for thyroid-stimulating hormone (TSH) radioimmunoassay test. The TSH test utilizes an immunological reaction in which labeled and unlabeled TSH molecules compete for binding sites on a specific antibody molecule. The Centria System utilizes centrifugal force to mix the difference reagents at the same time and after incubation to separate the bound and free antigen through the columns containing a second antibody on the solid-phase supports of this invention. The retaining means or disc in the bottom of the column is of such a porosity and composition that all of the fluid transferred remains in the column for absorption. Only upon increasing the centrifugal force above that required to transfer the fluids from the disc will liquid pass out of the column.

The following examples are illustrative:

EXAMPLE 1

Aqueous Standard Curve with Polyacrylamide Immobilized Angiotensin I Antiserum

A quantity of dry polyacrylamide entrapped angiotensin I antiserum sufficient to bind approximately fifty percent of the antigen tracer was transferred into polystyrene columns fitted with water impermeable polyethylene discs at the base. A 100 $\mu$l aliquot of angiotensin I-($^{125}$I) diluted in tris-acetate buffer (0.1 M, pH 7.4, containing 0.1% bovine serum albumin) to give approximately 20,000 cpm per 100 $\mu$l was pipetted manually into the outer cavity of the Centria System transfer disk. Standards of angiotensin I containing from 100 to 0 ng/ml in tris-acetate buffer were prepared and a 300 $\mu$l aliquot of each standard concentration was pipetted in duplicate into appropriate outer cavities of the transfer disc. The columns containing the gel entrapped antiserum were fitted into test tubes and positioned in the Centria System Incubator/Separator module along with the transfer disk. A 15 second centrifugation on the system transferred the 400 $\mu$l of solution into the columns.

Following a 15 minute incubation, high speed centrifugation was begun and 4 ml/tube of tris-acetate buffer were added to the transfer disk providing a fast, simultaneous elution of the unbound tracer from the gels. The elution solution containing the unbound angiotensin I-($^{125}$I) was collected in tubes beneath each column and counted on the Centria System tri-well gamma counting module. The columns were also counted to determine the bound fraction.

$$B/T = \frac{\text{Counts in the column (Bound)}}{\text{Counts in the column (Bound) + Counts eluted (Free)}}$$

% Bound = $B/T \times 100\%$ $$B/B_o = \frac{\% \text{ Bound for each standard}}{\% \text{ Bound when the standard concentration in the incubate}} = 0 \text{ ng/ml}$$

A dose-response curve was generated from the data and plotted on semilog paper. Nonspecific binding of the antigen to the gel and column was determined by entrapping normal rabbit serum in the polyacrylamide matrix and incubating and eluting it similarly. It was found to be <4%.

EXAMPLE 2

Automated Assay for Cortisol Utilizing a Heat Pretreatment Step

Cortisol standards were prepared by initially diluting cortisol in 95% ethanol then in 0.1 M sodium phosphate buffer (pH 7.4, 0.05% Tween 20). These standards were in turn diluted in serum pretreated with charcoal to remove endogenous cortisol. Clinical samples were diluted along with the serum based standards in a denaturation buffer (90% 0.1 M sodium phosphate at pH 7.4 containing 0.05% Tween 20, 10% methanol) and heated at 60° for 30 minutes to destroy cortisol binding globulin (CBG).

After the heat pretreatment step, the standards and samples were pipetted onto the transfer disk of the Centria System along with radiolabeled cortisol and buffer (0.1 M sodium phosphate containing 0.05% Tween 20 at pH 7.4) for a total volume of 350 µl. The contents of the disk were transferred to the ring of tubes supporting the columns containing polyacrylamide entrapped cortisol antiserum. Following a 15 minute incubation, the unbound fraction of labeled cortisol was removed by rinsing, as above, with 4 ml/tube of the phosphate/Tween buffer. The columns and tubes were counted on the Centria System tri-well counter and the data thus generated used to construct a standard curve.

Clinical samples evaluated by this procedure showed a good correlation with expected values, especially when compared to data obtained by a solution phase assay with the same antiserum.

EXAMPLE 3

Automated Assay for Cortisol Utilizing a Proteolytic Enzyme to Destroy CBG

The assay was conducted in the same manner as described in the example above except for the elimination of the heat treatment step and denaturation buffer. Inactivation of the cortisol binding globulins took place in the wells of the transfer disk when 150 µl of a pepsin solution (4 mg/ml in 0.14 N HCl, 4100 units/mg), 50 µl serum based cortisol standard, 100 µl tracer and 50 µl 0.1 M sodium phosphate buffer (pH 7.4 0.05% Tween 20) were preincubated for approximately 5 minutes, prior to transfer to the columns containing polyacrylamide entrapped cortisol antiserum.

Control sera assayed by this technique correlated with the expected values. Recovery, parallelism and assay protein dependency studies also gave excellent results.

EXAMPLE 4

SPRIA in Column Reactor/Separator-Development of an Aqueous Standard Curve for Cortisol A polystyrene column is fitted with a porous semipermeable disc of polyethylene prior to the introduction of one ml of cortisol antiserum diluted in 0.1 M sodium phosphate buffer at pH 7.4. Following one to two hours incubation with the antiserum solution, the column is aspirated free of unadsorbed antiserum. Normal saline (1.5 ml) is added to the column and immediately aspirated. The saline rinsing procedure is repeated, then the column is filled with 0.5 % bovine serum albumin (BSA)-saline solution. Following a brief incubation with the BSA solution (10–30 minutes) the column is aspirated and air dried. The column, having the immobilized antiserum contained on its inner wall, can be used immediately for assay of cortisol or may be stored dessicated at ambient temperature and used within 2-3 months.

A standard curve for cortisol is generated either manually or with the aid of the Centria System Incubator/Separator and pipettor modules. Cortisol- ($^{125}$I), label, standard "known" amounts of cortisol and 0.1 M sodium phosphate (pH 7.4) buffer to equal 1.0 ml total are pipetted into cavities of the Centria transfer disk. The antibody coated columns are fitted into test tubes and placed with the transfer disk into the Centria System Incubator/Separator module. A fifteen second centrifugation, transfers the 1 ml reaction components to the antibody coated columns, where static incubation occurs. After 1-2 hours, the columns are centrifuged while 2 ml per tube 0.1 M sodium phosphate buffer is added to rinse the column free of unbound tracer. The buffer, carrying the unbound tracer, is collected in the tubes supporting the columns. The Centria gamma counter is used to monitor the bound cortisol-($^{125}$I) in the tubes. Non-specific binding (NSB) of the tracer to the polystyrene column surface is determined by eliminating the antiserum incubation and treating one column with BSA only.

The results are computed as described above. From these values a standard curve is plotted, % bound vs. concentration of cortisol in each standard.

EXAMPLE 5

Affinity Chromatographic Separation of Cortisol Antiserum From Serum Proteins

A quantity of cortisol covalently linked to Sepharose-4-B is placed into a polystyrene column fitted with a polyethylene disc and positioned on the Centria Incubator/Separator. Crude cortisol antiserum (100 µl) diluted with 300 µl of 0.1 M sodium phosphate buffer, pH 7.4 is added to the column reactor/separator containing the immobilized hapten. After a suitable period of time, the column is centrifuged and simultaneously eluted with buffer to remove the unbound fraction. The serum proteins and unbound components collected in the tubes supporting the columns are removed. Clean test tubes are put in place and the process is repeated, substituting an acid or chaotropic solution for the phosphate buffer. After the centrifugal elution, the cortisol antiserum is recovered from test tubes.

Although the invention has been illustrated by the foregoing examples, it is not to be construed as being limited to the materials employed therein, but rather, the invention encompasses the generic area as hereinbefore disclosed. Various modifications and embodiments of this invention can be made without departing from the spirit and scope thereof.

What is claimed is:

1. A reactor/separator device for use in rapid, automated solid phase immunoassays wherein components are mixed, transferred and separated by means of centrifugal force, said device comprised of, in combination, (a) a column which is open at both ends, (b) a retaining and filtering means disposed in said column and which is impermeable to aqueous solutions at approximately atmospheric pressure, but permeable to aqueous solutions when subjected to a centrifugal force, (c) a reaction and separation chamber disposed in said column above said filtering means and containing at least one matrix having immobilized therein an antigen or antibody component for the separation of at least one of said components of an antigen-antibody system.

2. The device of claim 1 wherein said column is cylindrical in shape and has a middle portion of essentially uniform diameter, a bottom portion which tapers to a lesser diameter than said middle portion, and an upper portion which is of a greater diameter than said middle portion, said retaining and filtering means being disposed within said column at a point wherein said middle portion narrows to said lesser diameter.

3. The device of claim 1 wherein said retaining and filtering means is in the form of a disc.

4. The device of claim 3 wherein said disc is comprised of a porous polyethylene material.

5. The device of claim 3 wherein said disc has porosity of from about 25 to about 150 microns.

6. The device of claim 1 wherein said matrix is present in said reaction and separation chamber as a powder.

7. The device of claim 1 wherein said matrix is present in said reaction and separation chamber as a tablet which upon contact with a solution swells and conforms to the configuration of said columns.

8. The device of claim 1 wherein said matrix is contained on the inner wall of said reaction and separation chamber.

9. In an immunoassay employing an antigen-antibody system and wherein samples and reagents are mixed and transferred by means of centrifugal force, the improvement which comprises transferring said samples and reagents to the reactor/separator device of claim 1, permitting said samples and reagents to incubate on said matrix, and separating therefrom at least one component of the antigen-antibody system.

* * * * *